United States Patent
Warman et al.

(10) Patent No.: US 7,280,869 B2
(45) Date of Patent: Oct. 9, 2007

(54) ARRHYTHMIA TERMINATION DETECTION BASED ON BEAT PATTERN

(75) Inventors: Eduardo N. Warman, Maple Grove, MN (US); Jacob D. Feala, San Diego, CA (US)

(73) Assignee: Medtronic, Inc., Minneapolis, MN (US)

( * ) Notice: Subject to any disclaimer, the term of this patent is extended or adjusted under 35 U.S.C. 154(b) by 235 days.

(21) Appl. No.: 11/004,072

(22) Filed: Dec. 3, 2004

(65) Prior Publication Data

US 2006/0122650 A1 Jun. 8, 2006

(51) Int. Cl.
*A61N 1/362* (2006.01)

(52) U.S. Cl. .......................... 607/14; 607/25; 600/515; 600/516

(58) Field of Classification Search ................ 600/515, 600/516, 518, 521; 607/14, 25
See application file for complete search history.

(56) References Cited

U.S. PATENT DOCUMENTS

| | | | |
|---|---|---|---|
| 5,243,980 A * | 9/1993 | Mehra | 607/6 |
| 5,554,175 A | 9/1996 | Alferness | 607/5 |
| 5,755,736 A * | 5/1998 | Gillberg et al. | 607/4 |
| 5,846,263 A | 12/1998 | Peterson et al. | 607/14 |
| 5,893,882 A | 4/1999 | Peterson et al. | |
| 5,931,857 A | 8/1999 | Prieve et al. | 607/14 |
| 5,987,356 A | 11/1999 | DeGroot | 607/5 |
| 6,178,350 B1 | 1/2001 | Olson et al. | 607/4 |
| 6,718,204 B2 | 4/2004 | DeGroot et al. | 607/4 |
| 2004/0064160 A1 | 4/2004 | Hettrick et al. | 607/14 |
| 2004/0171959 A1 * | 9/2004 | Stadler et al. | 600/518 |

FOREIGN PATENT DOCUMENTS

| | | |
|---|---|---|
| WO | WO9743002 | 11/1997 |
| WO | WO2004028364 | 4/2004 |

* cited by examiner

*Primary Examiner*—Carl Layno
*Assistant Examiner*—Brian T. Gedeon
(74) *Attorney, Agent, or Firm*—Michael C. Soldner; Girma Wolde-Michael

(57) ABSTRACT

In general, the invention is directed to an apparatus and method for determining whether an identified atrial tachyarrhythmia episode has terminated. The invention enables determination of whether the tachyarrhythmia episode has terminated based on cardiac beat pattern. In some embodiments of the invention, the determination as to whether the episode has terminated is made irrespective of the rate of atrial depolarizations.

28 Claims, 5 Drawing Sheets

ARRHYTHMIA TERMINATION DETECTION BASED ON BEAT PATTERN

TECHNICAL FIELD

The invention relates to cardiac pacing systems and, more particularly, to systems for delivering therapies to treat arrhythmias.

BACKGROUND

An arrhythmia is a disturbance in the normal rate, rhythm or conduction of the heartbeat. A tachyarrhythmia is a condition in which an arrhythmia occurs at a high rate. Arrhythmias are classified broadly based on the chamber of the heart in which the arrhythmia originates. Such classification includes supraventricular or atrial tachyarrhythmia, ventricular tachyarrhythmia, or concomitant supraventricular and ventricular tachyarrhythmia.

A conventional implantable medical device (IMD) generally detects an atrial tachyarrhythmia by analyzing the rate of atrial depolarizations or the time interval between atrial depolarizations. A higher rate of atrial excitation generally indicates a shorter interval between depolarizations. When, for example, a patient's atria activate so frequently that the time between depolarizations is below a predetermined atrial tachycardia detection interval (ATDI), the IMD identifies the event as an atrial tachyarrhythmia.

Conventional therapies for atrial tachyarrhythmias include anti-tachycardia pacing (ATP), cardioversion or defibrillation. ATP involves the application of a train of high rate pulses to the heart to restore a normal rhythm. Cardioversion and defibrillation both involve the application of high-energy pulses to the heart to restore a normal rhythm.

A conventional IMD operates to terminate an episode of atrial tachyarrhythmia in response to a detected rate of atrial depolarizations, or equivalently, in response to a detected abnormal interval between depolarizations. When a conventional IMD detects that the median atrial activation interval is above the ATDI, for example, the IMD delivers a therapy in attempt to terminate the atrial tachyarrhythmia episode. In some instances, the IMD processor may erroneously indicate that the episode is terminated subsequent to the delivery of therapy when the episode of atrial tachyarrhythmia may not have been terminated, even if the median atrial activation interval is above the ATDI.

SUMMARY

In general, the invention is directed to apparatuses and methods for determining whether an identified atrial tachyarrhythmia episode has terminated. More particularly, subsequent to an atrial tachyarrhythmia episode, the invention provides for determination of whether the episode has terminated as a function of a beat pattern. The beat pattern depends upon the timing of one or more atrial depolarizations during an R-R interval, and hence represents a sequence and timing of atrial and ventricular depolarizations.

The IMD processor terminates the atrial tachyarrhythmia episode indicating that a current episode has expired based on the beat pattern. In the present invention, the atrial tachyarrhythmia episode may be terminated irrespective of the rate of atrial depolarizations. Thus, an erroneous termination of an atrial tachyarrhythmia episode could be avoided.

The IMD detects the onset of an atrial tachyarrhythmia episode as a function of atrial depolarization rate, beat pattern, or any combination thereof. The criteria used to identify termination of the atrial tachyarrhythmia episode may be different than the one used to determine onset.

In some cases, the rate of atrial depolarization increases, and the time interval between atrial depolarizations may fall below a programmed ATDI value. At some point, the rate of atrial depolarizations in a beat pattern may decrease to a point where the time interval rises above the ATDI.

The IMD of the present invention evaluates the beat pattern when determining whether to terminate the atrial tachyarrhythmia episode. If the beat pattern is symptomatic of tachyarrhythmia, the IMD does not terminate the episode, even if the rate of atrial depolarization exceeds the ATDI threshold. Instead, the IMD records an ongoing episode. Upon subsequent interrogation of the IMD, a physician can evaluate the episode and determine whether to adjust any of the IMD parameters pertaining to delivery of anti-tachyarrhythmia therapy. In some cases, the physician may adjust the ATDI.

The IMD can be configured to generate beat pattern information from tracked atrial and ventricular events. The IMD uses the beat pattern information to determine whether the heart rhythm indicates termination of the identified tachyarrhythmia episode. One example of a beat pattern indicating atrial tachyarrhythmia is a waveform that shows more than one atrial activation in correlation with a complementary ventricular activation. In normal sinus rhythm, a single atrial activation is accompanied by a subsequent single ventricular activation, yielding a 1:1 ratio of atrial to ventricular activations. A higher ratio, such as a 2:1 ratio, is indicative of atrial tachyarrhythmia.

Another example of a beat pattern that is symptomatic of atrial tachyarrhythmia is a waveform that indicates retrograde conduction. In some embodiments, the IMD monitors the R-R interval that represents successive ventricular depolarizations, and determines whether the atrial depolarizations occur in the first half or the second half of the R-R interval. An atrial depolarization that occurs in the first half of the R-R interval is classified as retrograde conduction.

In one embodiment, the invention is directed to a method comprising detecting a beat pattern associated with a heart rhythm of a patient. The beat pattern represents a sequence of atrial and ventricular depolarizations within an R-R interval, and the invention enables determining whether a detected atrial tachyarrhythmia episode has terminated as a function of the beat pattern.

In another embodiment, the invention is directed to an implantable medical device comprising a processor programmed to detect a beat pattern associated with a heart rhythm of a patient. The beat pattern indicates a sequence of atrial and ventricular depolarizations within an R-R interval, and the processor determines whether a detected atrial tachyarrhythmia episode has terminated as a function of the beat pattern.

Further embodiments of the invention include one or more computer-readable media comprising instructions that cause a processor to carry out any of the methods of the invention.

In an additional embodiment, the invention is directed to an implantable medical device comprising one or more sensors configured to detect atrial and ventricular depolarizations, a memory, and a processor to detect a beat pattern associated with the atrial and ventricular depolarizations, determine whether a detected atrial tachyarrhythmia episode has terminated as a function of the beat pattern, and store information in the memory relating to termination of the episode.

The details of one or more embodiments of the invention are set forth in the accompanying drawings and the description below. Other features, objects, and aspects of the invention will be apparent from the description and drawings, and from the claims.

BRIEF DESCRIPTION OF DRAWINGS

Aspects of the present invention will be readily appreciated as they become better understood by reference to the following detailed description when considered in connection with the accompanying drawings, wherein.

DETAILED DESCRIPTION

Figure 1:
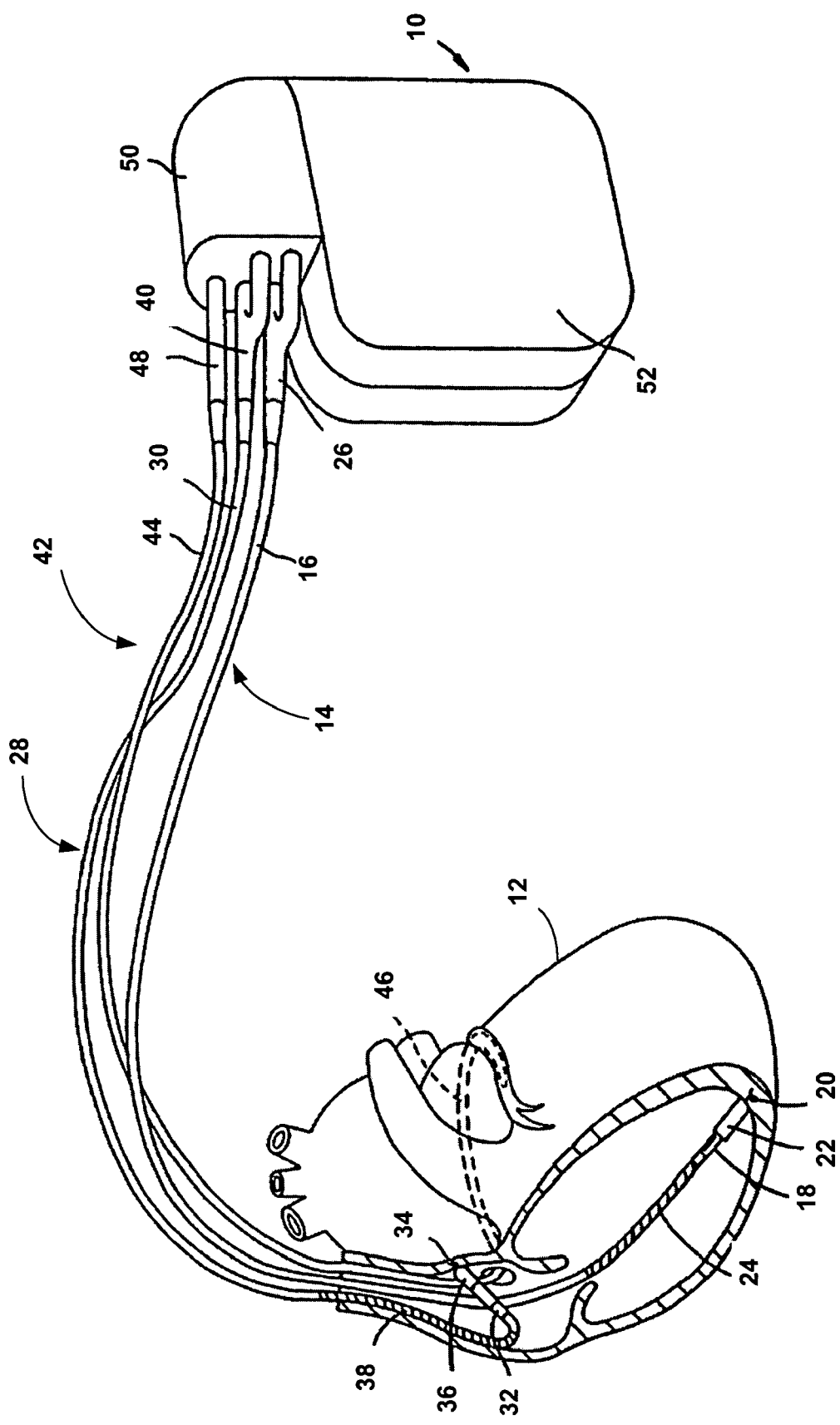
FIG. 1 is a diagram illustrating an implanted medical device that can deliver anti-tachyarrhythmia therapies and apply the techniques of invention.

FIG. 1 is a diagram illustrating an implanted medical device (IMD) 10 configured to deliver anti-tachyarrhythmia therapies. IMD 10, shown in conjunction with a human heart 12, can be configured to deliver anti-tachycardia pacing (ATP) therapy as well as cardioversion and defibrillation shocks, and monitor the effect of the delivered therapy. IMD 10 is configured to determine whether an atrial tachyarrhythmia episode has commenced, and is further configured to determine whether the atrial tachyarrhythmia episode has terminated as a function of a beat pattern associated with a rhythm of heart 12.

In general, the term "beat pattern" refers to the sequence and timing of atrial depolarizations within an R-R interval, and hence the relationship of atrial and ventricular events with respect to one another. In particular, a "beat pattern" depends upon the timing of one or more atrial depolarizations during an R-R interval. The beat pattern associated with a normal sinus rhythm generally includes one atrial activation per ventricular activation, and hence one atrial depolarization per R-R interval. In addition, the beat pattern associated with a normal sinus rhythm generally includes the atrial depolarization in the second half of the R-R interval. A beat pattern can be detected in many ways, such as by morphological analysis of the electrical signals accompanying the depolarizations, or by monitoring the timing of the depolarizations.

IMD 10 is configured to track atrial and ventricular events and detect a beat pattern as a function of the atrial and ventricular events. IMD 10 uses the detected beat pattern to determine whether the heart rhythm indicates termination of an atrial tachyarrhythmia episode that had been previously detected. Beat patterns that indicate an ongoing episode of atrial tachyarrhythmia include a beat pattern that has more than one atrial activation per ventricular activation, or a beat pattern that indicates retrograde conduction by the occurrence of an atrial depolarization in the first half of the R-R interval.

The invention is not limited to detection of the particular beat patterns described above. Rather, the invention encompasses detection of other beat patterns that are a function of the timing of at least one atrial depolarization during an R-R interval. For example, IMD 10 can parse an R-R interval into more than a first and second half. In one exemplary embodiment, IMD 10 parses an R-R interval into three or more zones, and assigns a "pattern code" as a function of the zone or zones in which one or more atrial activations occur. A beat pattern may take into consideration such a pattern code, but is not required to do so.

IMD 10 utilizes beat pattern data to determine the status of the atrial tachyarrhythmia episode based on a beat pattern associated with a heart rhythm. In one embodiment of the invention, IMD 10 determines the status of the atrial tachyarrhythmia episode irrespective of the rate of atrial depolarizations. In such an embodiment, the rate of atrial depolarization is irrelevant to the question of whether the atrial tachyarrhythmia episode has terminated.

IMD 10 detects an onset of an atrial tachyarrhythmia episode and a beat pattern via one of more leads deployed in heart 12. In exemplary system shown in FIG. 1, a ventricular lead 14 having an elongated insulative lead body 16 enclosing one or more coiled conductors is deployed in the right ventricle of heart 12. The distal end of ventricular lead 14 includes a ring electrode 18, an extendable helix electrode 20, mounted retractably within an insulative electrode head 22 and an elongated coil electrode 24. Each of electrodes 18, 20, and 24 is coupled to one of the coiled conductors within lead body 16. Electrodes 18 and 20 can be used for both cardiac pacing and sensing of ventricular depolarizations. Electrode 24 is configured to deliver defibrillation or cardioversion shocks to the right ventricle. At the proximal end of ventricular lead 14 is a bifurcated connector 26 that couples to connector block 50 of IMD 10.

An atrial lead 28 includes an elongated insulative lead body 30, enclosing one or more coiled conductors. The J-shaped distal end of atrial lead 28 includes a ring electrode 32 and an extendable helix electrode 34, mounted retractably within an insulative electrode head 36 and an elongated coil electrode 38. Each of electrodes 32, 34, and 38 is coupled to one of the coiled conductors within lead body 30. Electrodes 32 and 34 can be employed for atrial pacing, including anti-tachyarrhythmia pacing, and for sensing atrial depolarizations. Elongated coil electrode 38 is configured to deliver defibrillation or cardioversion shocks to the right atrium. At the proximal end of lead 28 is a bifurcated connector 40 that couples to connector block 50 of IMD 10.

In the embodiment shown in FIG. 1, a third lead 42 is deployed in the coronary sinus and great vein of heart 12. Coronary sinus lead 42 includes an elongated insulative lead body 44. The distal end of lead 42 includes an elongated coiled defibrillation electrode 46. The proximal end of lead 42 includes a connector 48 that carries an electrical connector that couples to connector block 50 of IMD 10.

The system depicted in FIG. 1 is exemplary of a system that can implement the invention, and the invention is not limited to the particular system or structure shown. The invention may be practiced, for example, with an IMD that omits coronary sinus lead 42. The invention may also be practiced with unipolar leads, in which the return current path for electrical stimulation includes the housing 52 of the IMD.

Figure 2:
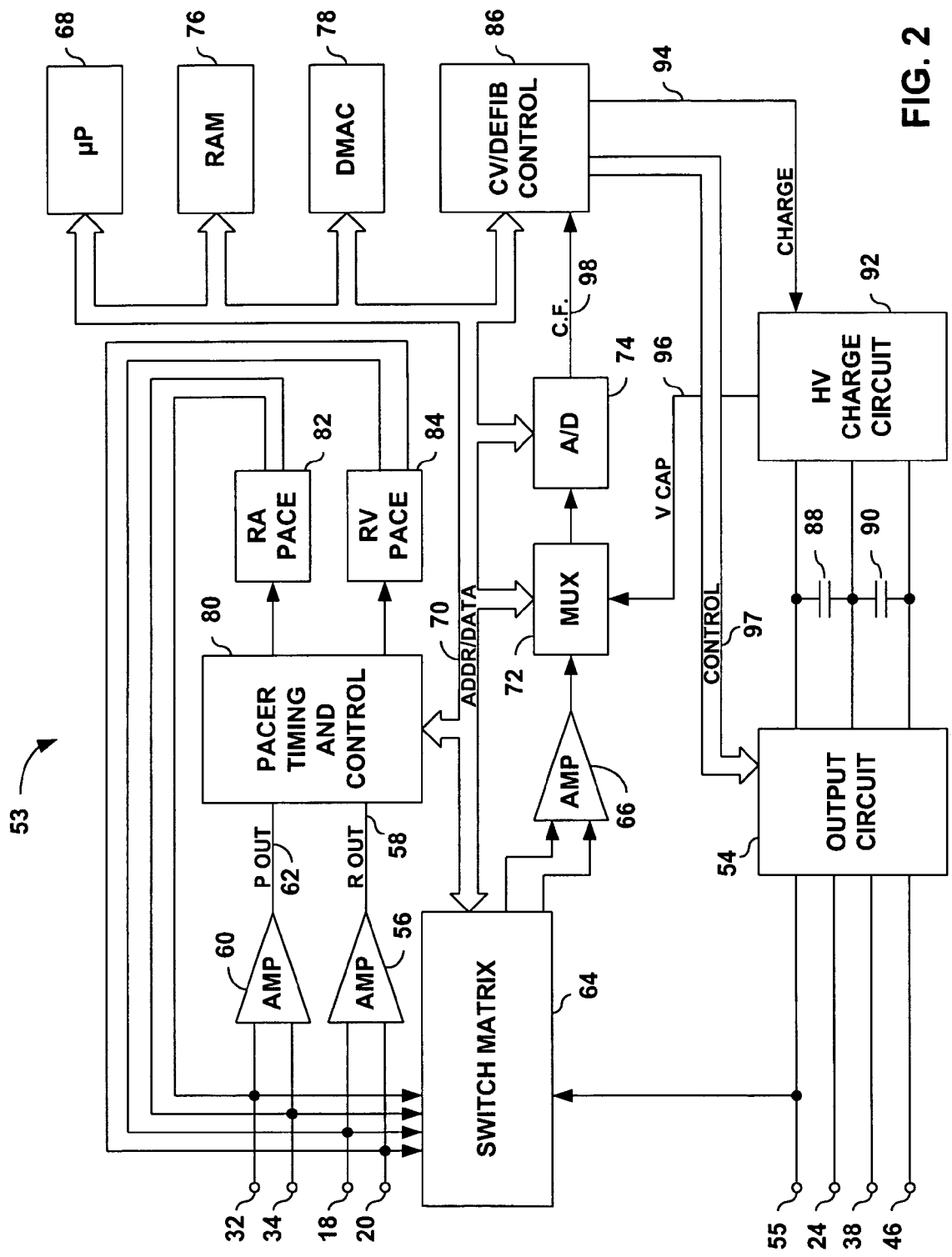
FIG. 2 is a functional schematic diagram illustrating a system capable of delivering anti-tachyarrhythmia therapies such as ATP therapies and applying the techniques of invention.

FIG. 2 is a functional schematic diagram illustrating a system 53 that can be implemented by the system depicted in FIG. 1. Although system 53 is configured to carry out the techniques of the invention, the invention is not limited to the system shown. In particular, system 53 is configured to detect an atrial tachyarrhythmia episode, to deliver anti-tachyarrhythmia therapies such as ATP, defibrillation or cardioversion, to detect a beat pattern, and to determine whether the atrial tachyarrhythmia episode has terminated as a function of the beat pattern.

In the example of FIG. 2, electrode 55 represents the uninsulated portion of the housing 52 of IMD 10. Electrodes 24, 38, 46, and 55 are coupled to high voltage output circuit 54. Electrodes 18 and 20 are coupled to R-wave amplifier 56, which can take the form of an automatic gain controlled amplifier providing an adjustable sensing threshold as a function of the measured R-wave amplitude. A signal is generated on R-out line 58 whenever the signal sensed between electrodes 18 and 20 exceeds the present sensing threshold. R-wave amplifier 56 is an example of a detector configured to detect ventricular depolarizations sensed via electrodes 18 and 20.

Electrodes 32 and 34 are coupled to a P-wave amplifier 60, which also may take the form of an automatic gain controlled amplifier providing an adjustable sensing threshold as a function of the measured P-wave amplitude. A signal is generated on P-out line 62 when the signal sensed between electrodes 32 and 34 exceeds the sensing threshold. P-wave amplifier 60 is an example of a detector configured to detect atrial depolarizations sensed via electrodes 32 and 34.

Switch matrix 64 selects which electrodes are coupled to wide band amplifier 66 for use in digital signal processing. Selection of electrodes is controlled by a controller, which may take the form of microprocessor 68. Microprocessor 68 controls selection of electrodes by switch matrix 64 via data/address bus 70. Signals from the electrodes selected for coupling to amplifier 66, also called electrogram signals, are provided to multiplexer 72 and are thereafter converted to multi-bit digital signals by A/D converter 74, for storage in memory, such as random access memory (RAM) 76, under control of direct memory access circuit (DMAC) 78.

In some embodiments, microprocessor 68 is programmed to employ digital signal processing techniques to characterize the digitized signals stored in RAM 76 to recognize and classify the heart rhythm using any of a variety of known signal processing methods. Microprocessor 68, in some embodiments, can be configured to perform one or more morphological analyses on the signals to evaluate the shapes or morphologies of the signals. Morphological analyses include any analyses of the signal morphologies, including but not limited to Fourier and wavelet analyses. In addition, microprocessor 68 receives information about the timing of atrial and ventricular depolarizations via pacer timing/control circuitry 80.

Microprocessor 68 may detect an onset of an atrial tachyarrhythmia episode by, for example, monitoring the rate of atrial depolarizations. In one embodiment, microprocessor 68 determines that an atrial tachyarrhythmia episode has begun when the mean or median time between atrial depolarizations falls below a programmed ATDI stored in memory 76. In some embodiments, microprocessor 68 further detects a beat pattern and determines whether the atrial tachyarrhythmia episode has begun as a function of the beat pattern. In addition, microprocessor 68 determines whether the atrial tachyarrhythmia episode has terminated as a function of the beat pattern. Microprocessor 68 identifies beat patterns from the sequence of atrial and ventricular depolarizations within an R-R interval and the timings of the depolarizations.

Additionally, microprocessor 68 controls delivery of therapy to the patient. Therapy can include anti-tachyarrhythmia pacing controlled by pacer and timing circuitry 80 and administered to the atria and ventricle via output circuits 82 and 84. Pacer and timing circuitry 80 and output circuit 82 are one example of a therapy module that can be configured to administer anti-tachyarrhythmia therapy during the atrial tachyarrhythmia episode. In some embodiments, microprocessor 68 selects among several anti-tachyarrhythmia pacing regimens.

In the embodiment depicted in FIG. 2, microprocessor 68 may operate to control the delivery of cardioversion and defibrillation shocks to arrest atrial tachyarrhythmia. In response to the detection of atrial or ventricular fibrillation or tachyarrhythmia needing a cardioversion shock, microprocessor 68 activates cardioversion/defibrillation control circuitry 86, which initiates charging of the high voltage capacitors 88 and 90 via charging circuit 92, under control of high voltage charging control line 94. The voltage on high voltage capacitors 88, 90 is monitored via VCAP line 96, which is passed through multiplexer 72 and in response to reaching a predetermined value set by microprocessor 68, results in generation of a logic signal on Cap Full (CF) line 98, terminating charging. Thereafter, timing of the delivery of the defibrillation or cardioversion shock is controlled by circuitry 86 via control bus 97. Control circuitry 86, charging circuit 92, capacitors 88 and 90, and output circuit 54 comprise another example of a therapy module that can be configured to administer anti-tachyarrhythmia therapy during the atrial tachyarrhythmia episode.

Various therapy regimens may be needed to terminate a specific atrial tachyarrhythmia. In a typical embodiment of the invention, different therapies can be applied to terminate an episode. Microprocessor 68 detects a beat pattern and determines whether the episode has terminated as a function of the beat pattern. Although the various detection functions described herein are attributed to microprocessor 68, other processors may be implemented, either in digital or analog form, with circuitry to provide similar functionality.

In some cases, the rate of atrial depolarizations declines and the mean or median time between atrial depolarizations rises above the programmed ATDI. This may require that microprocessor 68 be programmed to discontinue anti-tachyarrhythmia therapy. Thus, the ATDI may serve as a "therapy threshold," and the determination as to whether or not to deliver therapy may depend upon whether the threshold is passed.

Satisfaction of the therapy threshold is not determinative of whether the episode has terminated. In other words, the fact that the time between atrial depolarizations has exceeded the ATDI is not determinative of whether the atrial tachyarrhythmia episode has terminated. Instead, microprocessor 68 relies on the beat pattern to determine whether the atrial tachyarrhythmia episode has actually terminated, avoiding false determinations that could arise from reliance on the therapy threshold alone. A beat pattern can reveal that the atrial tachyarrhythmia episode has not terminated, even though a rate-based analysis that relies on the therapy threshold would suggest that the arrhythmia is under control.

As an example, a beat pattern that includes more atrial activations than ventricular activations indicates a continuing atrial tachyarrhythmia episode, even though the rate of atrial activations may have declined. When microprocessor 68 detects a beat pattern that indicates that the atrial tachyarrhythmia episode has not terminated, microprocessor 68 stores information in memory 76 to indicate an ongoing episode. This information will be available at a later time for evaluation by a physician upon interrogation of IMD 10. In this manner, microprocessor 68 avoids storage of erroneous termination, providing the physician with more accurate information concerning the prevalence and duration of atrial tachyarrhythmia episodes. When a beat pattern indicates an ongoing episode of atrial tachyarrhythmia, despite the presence of a rhythm that exceeds the ATDI, the physician may conclude that the programmed ATDI is too brief. In this case, the physician may determine that the patient could benefit from a longer ATDI, and program IMD 10 accordingly.

Figure 3:
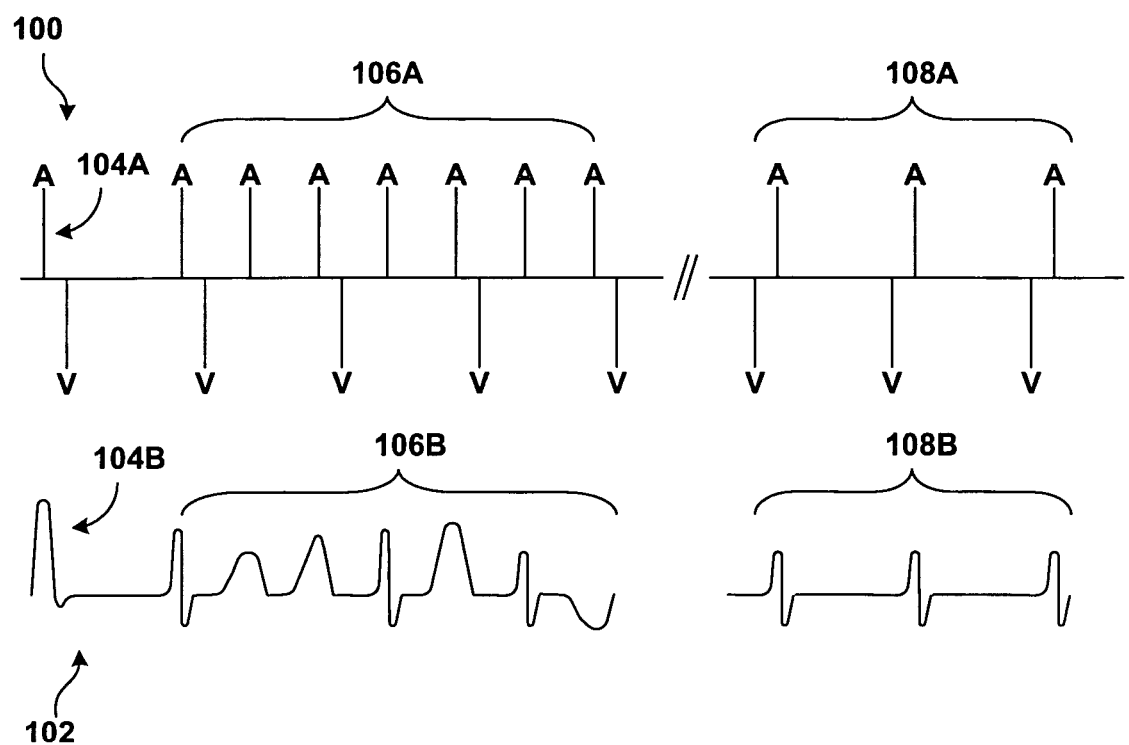
FIGS. 3-5 are marker channel diagrams showing an illustrative tachyarrhythmia episode and illustrating the techniques of the invention.

FIG. 3 is a marker channel diagram 100 and a corresponding atrial electrogram diagram 102 illustrating an exemplary tachyarrhythmia episode. The data in the diagrams of FIG. 3 represent detected atrial and ventricular depolarizations. This data may be generated by systems such as those depicted in FIGS. 1 and 2. In marker channel diagram 100, detected atrial depolarizations are presented above the horizontal line and designated with "A," and ventricular depolarization are presented below the horizontal line and designated with "V." The time interval between successive ventricular depolarizations is an R-R interval. Reference numeral 104A identifies a normal atrial activation, and reference numeral 106A identifies an episode of atrial tachycardia, in which there are more atrial depolarizations than ventricular depolarizations in a given R-R interval.

In atrial electrogram diagram 102, atrial depolarizations are presented as a series of rapid activations 106B, which correspond to activations 106A in marker channel diagram 100. In the example of FIG. 3, a normal activation 104B in atrial electrogram diagram 102 exhibits a normal morphology, and corresponds to a normal atrial activation 104A in marker channel diagram 100. In contrast to normal activation 104B, activations in tachycardia episode 106B demonstrate abnormal morphology in addition to a rapid rate of depolarization.

Marker channel diagram 100 and atrial electrogram diagram 102 each depict an abrupt increase in the frequency of atrial depolarizations. As depicted in FIG. 3, the frequency of atrial depolarizations is sufficiently high that the time interval between atrial depolarizations would ordinarily be less than the programmed ATDI. Furthermore, the beat pattern is inconsistent with a beat pattern that would accompany a normal elevation in heart rate, in that there are two atrial depolarizations for every ventricular depolarization, as shown by marker channel diagram 100. By identifying an excursion below the ATDI, a change in morphology, or both, microprocessor 68 detections the onset of an atrial tachyarrhythmia episode. Upon detection of an atrial tachyarrhythmia episode, microprocessor 68 may directs treatment designed to terminate the episode.

In FIG. 3, reference numeral 108A depicts a sequence of atrial and ventricular depolarizations at a later time following episode 106A, e.g., following delivery of anti-tachyarrhythmia therapy. Although the frequency of atrial depolarizations has decreased, and although the time interval between atrial depolarizations may be greater than the applicable ATDI, microprocessor 68 may nevertheless determine that the atrial tachyarrhythmia episode has not terminated, based upon the beat pattern. In making this determination, microprocessor 68 also may evaluate the morphology of the atrial activations.

In the example of FIG. 3, atrial depolarizations in sequence 108A occur in the first half of the R-R interval, which indicates retrograde conduction. The morphology of the activations shown in electrogram 102, however, could indicate that the arrhythmia is still ongoing and the episode of atrial tachyarrhythmia has not terminated. Microprocessor 68 stores data in memory indicating whether the episode has terminated. Microprocessor 68 may store in memory 76 a determination of the start and end of an atrial tachyarrhythmia episode, as well as all or some of the data on which the determination was made. Advantageously, the data stored by microprocessor 68 identifies episodes for which the rate of atrial depolarizations exceeded the ATDI, yet the beat pattern and morphology indicated ongoing atrial tachyarrhythmia. In this manner, analysis of the beat pattern and morphology promotes increased accuracy, avoiding erroneous termination indications that could otherwise be indicated by reliance on a threshold and rate-based analysis.

Figure 4:
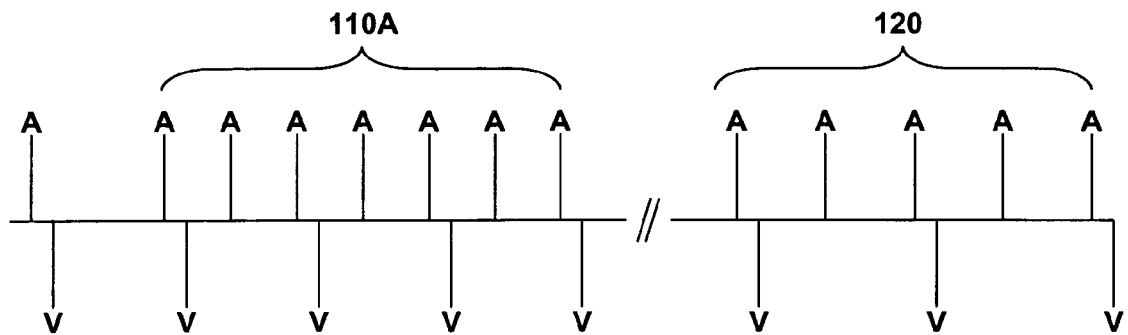

FIG. 4 is a marker channel diagram similar to FIG. 3, and depicts the onset of an episode 110A of atrial arrhythmia. In FIG. 4, reference number 120 depicts a sequence of atrial depolarizations with decreased frequency at a time following the initial onset of episode 110A, and following delivery of therapy in an attempt to terminate the episode. Assuming that the time interval between the atrial depolarizations in sequence 120 exceeds the ATDI due to the decreased frequency, microprocessor 68 nevertheless determines that the episode has not terminated, based upon the beat pattern. In particular, in sequence 120, there are clearly two atrial depolarizations for every ventricular depolarization, yielding an atrial to ventricular beat pattern of greater than 1:1. Hence, in this example, microprocessor 68 utilizes the beat pattern to identify an ongoing episode of atrial tachyarrhythmia and stores data in memory 76 to that effect.

Figure 5:
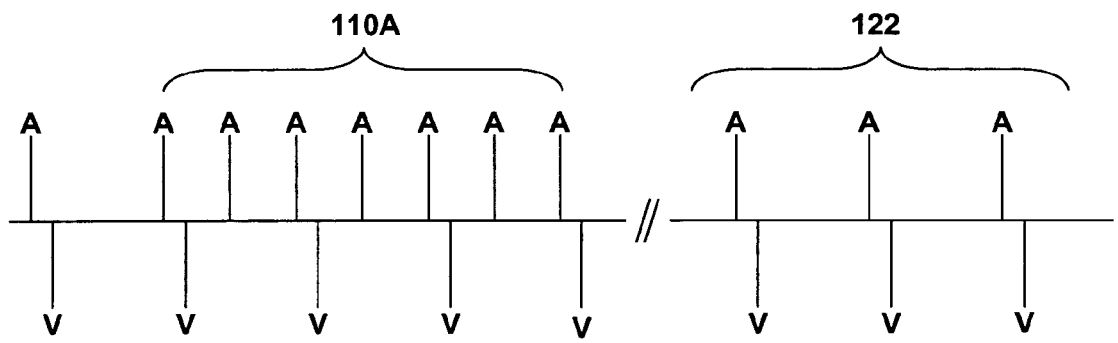

FIG. 5 is a marker channel diagram similar to FIGS. 3 and 4, and depicts the onset of an episode 111A of atrial arrhythmia identical to episode 110A of FIG. 4, for purposes of illustration. In FIG. 5, reference number 122 depicts a sequence 122 of atrial depolarizations with a lower frequency than sequence 120 of FIG. 4, at later time following delivery of atrial tachyarrhythmia therapy. Moreover, reference number 122 depicts a normal beat pattern. In this case, based on the beat pattern, microprocessor 68 determines that the episode 111A has terminated, and stores appropriate data in memory 76 for subsequent evaluation by a physician.

In the situations such as those depicted in FIGS. 4 and 5, microprocessor 68 also may analyze the morphology of an electrogram (not shown in FIG. 4 or 5) to properly identify either termination or an ongoing episode. For example, the normal beat pattern 122 of FIG. 5, accompanied by a normal P-wave morphology, would indicate that the episode had terminated. Consideration of both the beat pattern and morphology provides increased specificity and confidence in the final determination with respect to termination of the atrial tachyarrhythmia episode.

IMD 10 may be configured to determine that an atrial tachyarrhythmia episode has not terminated based upon a variety of beat patterns. In other words, the invention is not limited to the particular beat patterns described above. Furthermore, the invention may support application of additional criteria when classifying a beat pattern, such as a requirement that the beat pattern persist over a consecutive number of cardiac cycles.

Figure 6:
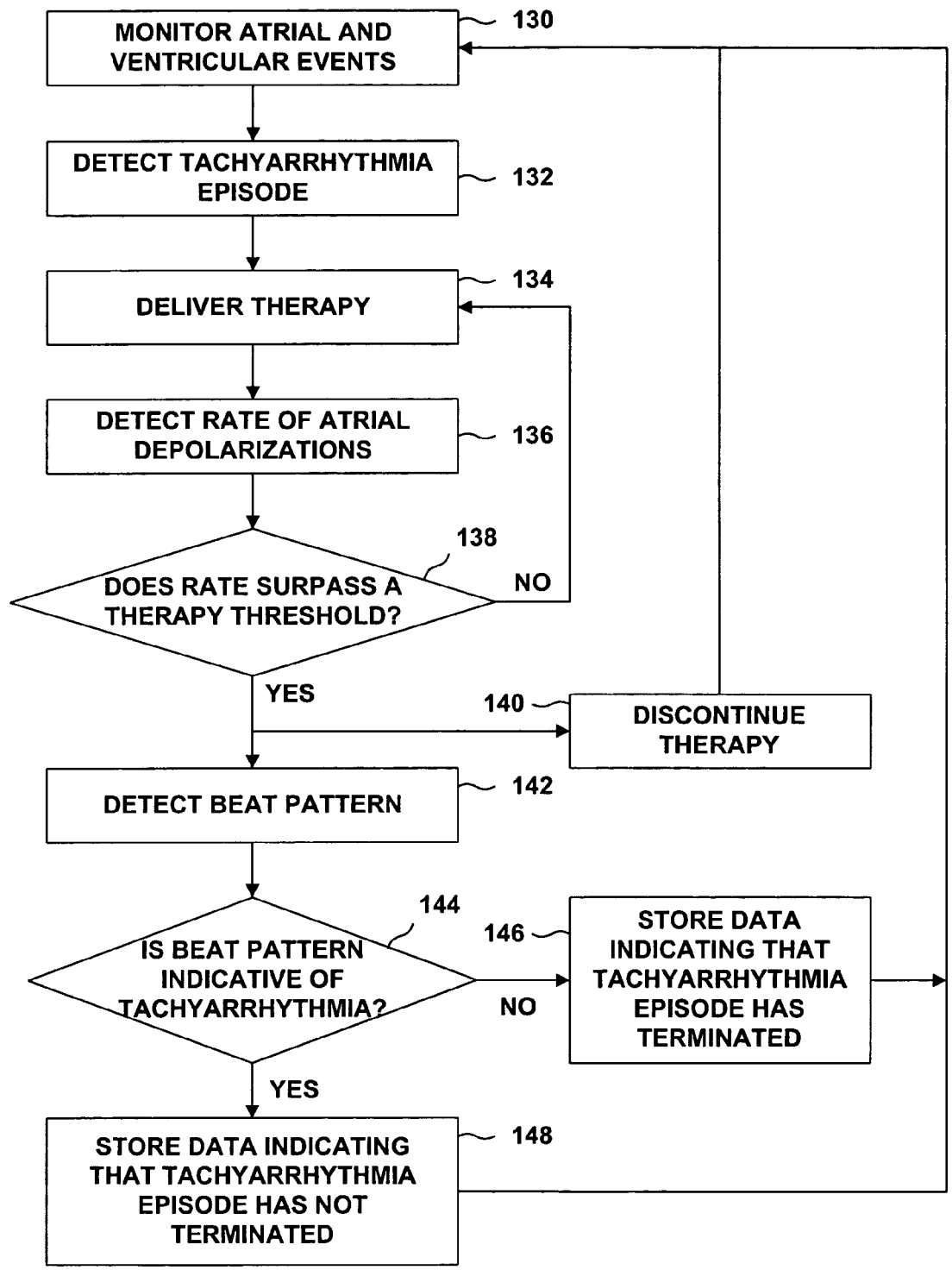
FIG. 6 is a flow diagram illustrating operation of an IMD according to one embodiment of the invention.

FIG. 6 is a flow diagram illustrating an example technique for detecting arrhythmia termination according to the invention. A medical device, such as IMD 10, monitors a patient's atrial and ventricular depolarizations (130) for indications of atrial tachyarrhythmia. IMD 10 detects an episode of atrial tachyarrhythmia (132) using any tachyarrhythmia detection technique. IMD 10 can be configured to administer therapy when indicated to address the episode (134), but the invention also supports embodiments in which IMD 10 detects an episode but administers no therapy. When IMD 10 administers therapy, IMD 10 monitors the response to the therapy by detecting the rate of atrial depolarizations (136). When the rate remains high and does not pass therapy threshold (138), such as when the interval between atrial depolarization remains less than the ATDI, IMD 10 continues to deliver therapy (134). In particular, IMD 10 continues to deliver the same therapy or tries a different therapy. When the rate passes the therapy threshold (138), IMD 10 discontinues the therapy (140) but does not necessarily determine that the episode has terminated.

IMD 10 detects a beat pattern associated with the heart rhythm of the patient (142) and determines whether the tachyarrhythmia episode has terminated as a function of the beat pattern (144). In the embodiment depicted in FIG. 6, IMD 10 makes the determination (144) without regard to the rate of atrial depolarizations, but the invention encompasses embodiments in which the IMD makes the determination (144) by taking into account the rate of atrial depolarizations. The invention also encompasses embodiments in which the IMD takes into account factors such as the P-R ratio or P-wave morphology when determining whether the tachyarrhythmia episode has terminated.

When the beat pattern is not indicative of tachyarrhythmia, IMD 10 in some embodiments stores data in memory 76 indicating that the episode has terminated (146). IMD 10 can store other data pertaining to the episode as well, such as time of onset, duration, therapy administered, and the response of the patient to the therapy.

When the beat pattern is indicative of ongoing tachyarrhythmia, IMD 10 can store data in memory 76 indicating that the episode has not terminated, even though the atrial activation interval is below a programmed ATDI (148). Once again, IMD 10 can store other data pertaining to the episode as well, such as time of onset, duration, therapy administered, and the response of the patient to the therapy. IMD 10 may also store the detected beat pattern. This storage of data (148) "flags" the episode for the physician, who may wish to consider adjusting the parameters of IMD 10. The physician could consider, for example, increasing the programmed ATDI.

The invention may offer several advantages over prior practice. For example, the invention helps the patient's physician learn about the efficacy of anti-tachyarrhythmia therapy. If the physician has programmed the ATDI to be too short, then the therapy might be terminated before the therapy has had full benefit. In particular, a rate-based analysis of the episode would suggest that the episode has been terminated, while a beat-pattern-based analysis would indicate that the episode has not been terminated (even though the rate of atrial depolarizations has declined). With this information, the physician can be made aware that slow atrial tachycardias might not be effectively treated. The physician can also use this information to adjust parameters of the IMD, such as the ATDI, to improve the efficacy of anti-tachyarrhythmia therapy.

In some IMDs, a patient's heart rhythm is subjected to a more advanced analysis when a tachyarrhythmia episode is detected. As discussed above, the invention supports embodiments in which the IMD takes morphological analysis into consideration when determining whether an episode has terminated, but advanced analysis can encompass additional analytical techniques as well. The invention further supports continuing the advanced analysis when the beat pattern indicates that the episode has not been terminated. This analysis may have diagnostic and therapeutic value.

As discussed previously, the invention supports embodiments in which the IMD detects an episode but administers no therapy. In those embodiments, the IMD can determine whether the episode has terminated by applying the techniques of the invention.

Various embodiments of the invention have been described. Various modifications may be made without departing from the scope of the claims. For example, the techniques of the invention can be applied to devices that provide no anti-tachyarrhythmia therapy, but monitor the effectiveness of anti-tachyarrhythmia therapies administered by other devices. The techniques of the invention can be also be applied by implantable devices that deliver therapies related to conditions other than or in addition to atrial tachyarrhythmia therapies, such as ventricular pacing or cardiac resynchronization.

Some of the techniques of the invention may be embodied as a computer-readable medium comprising instructions for a programmable processor such as microprocessor 68 in FIG. 2. The programmable processor may include one or more individual processors, which may act independently or in concert. A "computer-readable medium" includes but is not limited to read-only memory, Flash memory and a magnetic or optical storage medium. These and other embodiments are within the scope of the following claims.

What is claimed is:

1. A method comprising:
    detecting an atrial tachyarrhythmia episode in response to a rate corresponding to atrial depolarizations being less than a detection threshold;
    delivering a therapy in response to the detected atrial tachyarrhythmia episode;
    determining that the atrial tachyarrhythmia episode has terminated in response to the rate corresponding to subsequent atrial depolarizations being greater than the detection threshold;
    detecting, in response to the rate being greater than the detection threshold, a beat pattern associated with a heart rhythm of a patient, the beat pattern representing a sequence of atrial depolarizations and ventricular depolarizations; and
    confirming the determination that the detected atrial tachyarrhythmia episode has terminated as a function of the beat pattern.

2. The method of claim 1, wherein the confirming comprises determining the detected atrial tachyarrhythmia episode has not terminated when the beat pattern includes more than one atrial depolarization within an R-R interval.

3. The method of claim 1, wherein the confirming comprises determining the detected atrial tachyarrhythmia episode has not terminated when the beat pattern includes an atrial depolarization in a first half of an R-R interval.

4. The method of claim 1, wherein the confirming comprises determining the detected atrial tachyarrhythmia episode has terminated when the beat pattern includes a single atrial depolarization within an R-R interval and the single atrial depolarization is within a second half of the R-R interval.

5. The method of claim 1, wherein the confirming comprises determining the detected atrial tachyarrhythmia episode has terminated based on a morphology of the beat pattern.

6. The method of claim 1, further comprising:
    terminating delivery of the therapy when the rate of atrial depolarizations is greater than the detection threshold.

7. The method of claim 6, further comprising storing data in memory when the termination of the detected atrial tachyarrhythmia episode is not confirmed and when the rate of atrial depolarizations is less than the detection threshold.

8. An implantable medical device comprising a processor programmed to:
   detect an atrial tachyarrhythmia episode in response to a rate corresponding to atrial depolarizations being less than a detection threshold;
   deliver a therapy in response to the detected atrial tachyarrhythmia episode;
   determine that the atrial tachyarrhythmia episode has terminated in response to the rate corresponding to subsequent atrial depolarizations being greater than the detection threshold;
   detect, in response to the rate being greater than the detection threshold. a beat pattern associated with a heart rhythm of a patient, the beat pattern indicating a sequence of atrial depolarizations and ventricular depolarizations; and
   confirm the determination that the detected atrial tachyarrhythmia episode has terminated as a function of the beat pattern.

9. The device of claim 8, wherein the processor does not confirm the determination that the detected atrial tachyarrhythmia episode has terminated when the beat pattern includes more than one atrial depolarization within an R-R interval.

10. The device of claim 8, wherein the processor does not confirm the determination that the detected atrial tachyarrhythmia episode has terminated when the beat pattern includes an atrial depolarization in a first half of an R-R interval.

11. The device of claim 8, wherein the processor does not confirm the determination that the detected atrial tachyarrhythmia episode has terminated when the beat pattern includes a single atrial depolarization within an R-R interval, and the atrial depolarization is within a second half of the R-R interval.

12. The device of claim 8, wherein the processor a does not confirm the determination that the detected atrial tachyarrhythmia episode has terminated based on a morphology of the beat pattern.

13. The device of claim 11, further comprising an electrical pulse generator to deliver the therapy.

14. The device of claim 13, wherein the processor compares the rate of atrial depolarizations with the detection threshold, and controls the electrical pulse generator to discontinue delivery of the therapy when the rate of atrial depolarizations is greater than the detection threshold.

15. The device of claim 14, further comprising a memory, wherein the processor stores information in the memory to indicate when the termination of the detected atrial tachyarrhythmia episode is not confirmed and when the rate of atrial depolarizations is less than the detection threshold.

16. A computer-readable medium comprising instructions to cause a processor within an implantable medical device to:
   detect an atrial tachyarrhythmia episode in response to a rate corresponding to atrial depolarizations being less than a detection threshold;
   deliver a therapy in response to the detected atrial tachyarrhythmia episode;
   determine that the atrial tachyarrhythmia episode has terminated in response to the rate corresponding to subsequent atrial depolarizations being greater than the detection threshold;
   detect, in response to the rate being greater than the detection threshold, a beat pattern associated with a heart rhythm of a patient, the beat pattern representing a sequence of atrial depolarizations and ventricular depolarizations; and
   confirm the determination that the detected atrial tachyarrhythmia episode has terminated as a function of the beat pattern.

17. The computer-readable medium of claim 16, wherein the instructions cause the processor to not confirm that the detected atrial tachyarrhythmia episode has terminated when the beat pattern includes more than one atrial depolarization within an R-R interval.

18. The computer-readable medium of claim 16, wherein the instructions cause the processor to not confirm that the detected atrial tachyarrhythmia episode has terminated when the beat pattern includes an atrial depolarization in a first half of an R-R interval.

19. The computer-readable medium of claim 16, wherein the instructions cause the processor to confirm that the detected atrial tachyarrhythmia episode has terminated when the beat pattern includes a single atrial depolarization within an R-R interval and the atrial depolarization is within a second half of the R-R interval.

20. The computer-readable medium of claim 16, wherein the instructions cause the processor to confirm that the detected atrial tachyarrhythmia episode has terminated based on a morphology of the beat pattern.

21. The computer-readable medium of claim 16, wherein the instructions cause the processor to control an electrical pulse generator to deliver the therapy as a function of the rate of atrial depolarizations.

22. The computer-readable medium of claim 21, wherein the instructions cause the processor to
   control the electrical pulse generator to discontinue delivery of the anti-tachyarrhythmia therapy when the rate of atrial depolarizations is greater than the detection threshold.

23. The computer-readable medium of claim 22, wherein the instructions cause the processor to store data in a memory when the termination of the detected atrial tachyarrhythmia episode is not confirmed and when the rate of atrial depolarizations is less than the detection threshold.

24. An implantable medical device comprising:
   means for detecting an atrial tachyarrhythmia episode in response to a rate corresponding to atrial depolarizations being less than a detection threshold;
   means for applying an atrial tachyarrhythmia therapy in response to the detected atrial tachyarrhythmia episode;
   means for determining that the atrial tachyarrhythmia episode has terminated in response to the rate corresponding to subsequent atrial depolarizations being greater than the detection threshold;
   means for detecting, in response to the rate being greater than the detection threshold, a beat pattern associated with a heart rhythm of a patient, the beat pattern representing a sequence of atrial depolarizations and ventricular depolarizations; and
   means for confirming the determination that the detected tachyarrhythmia episode has terminated as a function of the beat pattern.

25. The device of claim 24, wherein the determination that the detected atrial tachyarrhythmia episode has terminated is not confirmed when the beat pattern includes more than one atrial depolarization within an R-R interval.

26. The device of claim 24, wherein the determination that the detected atrial tachyarrhythmia episode has terminated is not confirmed when the beat pattern includes an atrial depolarization in a first half of an R-R interval.

27. The device of claim 24, wherein the determination that the detected atrial tachyarrhythmia episode has terminated is confirmed when the beat pattern includes a single atrial depolarization within an R-R interval and the atrial depolarization is within a second half of the R-R interval.

28. An implantable medical device comprising:
- one or more electrodes configured to detect atrial depolarizations and ventricular depolarizations and to deliver an atrial tachyarrhythmia therapy in response to an atrial tachyarrhythmia episode;
- a memory; and
- a processor programmed to detect an atrial tachyarrhythmia episode in response to a rate corresponding to atrial depolarizations being less than a detection threshold, determine that the atrial tachyarrhythmia episode has terminated in response to the rate corresponding to subsequent atrial depolarizations being greater than the detection threshold, detect, in response to the rate being greater than the detection threshold, a beat pattern associated with the atrial and ventricular depolarizations, confirm the determination that the detected atrial tachyarrhythmia episode has terminated as a function of the beat pattern, and store information in the memory relating to the confirmation of the termination of the episode.

* * * * *